United States Patent
Phillips et al.

(10) Patent No.: US 6,860,850 B2
(45) Date of Patent: Mar. 1, 2005

(54) RETRACTOR BLADE CONNECTOR HEAD

(75) Inventors: Burns Phillips, Nashville, TN (US); Larry Griffith, Lakeville, MN (US)

(73) Assignee: BOSS Instruments Ltd., Nashville, TN (US)

(*) Notice: Subject to any disclaimer, the term of this patent is extended or adjusted under 35 U.S.C. 154(b) by 25 days.

(21) Appl. No.: 10/264,750

(22) Filed: Oct. 4, 2002

(65) Prior Publication Data

US 2003/0069478 A1 Apr. 10, 2003

Related U.S. Application Data

(60) Provisional application No. 60/327,437, filed on Oct. 5, 2001.

(51) Int. Cl.$^7$ ................................................ A61B 1/32
(52) U.S. Cl. ...................................... 600/227; 600/210
(58) Field of Search ................................ 600/201, 210, 600/213, 214, 219, 220, 225, 227, 228, 229

(56) References Cited

U.S. PATENT DOCUMENTS

| | | | | |
|---|---|---|---|---|
| 569,839 A | * | 10/1896 | Roeloffs | 600/213 |
| 2,688,173 A | * | 9/1954 | Peet | 24/704.1 |
| 3,749,088 A | * | 7/1973 | Kohlmann | 600/215 |
| 4,461,284 A | * | 7/1984 | Fackler | 600/228 |
| 4,896,661 A | * | 1/1990 | Bogert et al. | 606/86 |
| 5,013,314 A | * | 5/1991 | Firica et al. | 606/64 |
| 5,451,082 A | * | 9/1995 | Murai | 292/246 |
| 5,795,291 A | * | 8/1998 | Koros et al. | 600/232 |
| 5,846,193 A | * | 12/1998 | Wright | 600/215 |
| 5,882,298 A | * | 3/1999 | Sharratt | 600/213 |
| 5,931,777 A | * | 8/1999 | Sava | 600/213 |
| 5,984,865 A | * | 11/1999 | Farley et al. | 600/213 |
| 5,993,385 A | * | 11/1999 | Johnston et al. | 600/213 |
| 6,042,540 A | * | 3/2000 | Johnston et al. | 600/213 |
| D430,668 S | * | 9/2000 | Koros et al. | D24/135 |
| 6,206,826 B1 | * | 3/2001 | Mathews et al. | 600/210 |
| 6,340,345 B1 | * | 1/2002 | Lees et al. | 600/226 |
| 6,416,465 B2 | * | 7/2002 | Brau | 600/210 |

* cited by examiner

Primary Examiner—Eduardo C. Robert
Assistant Examiner—David Comstock
(74) Attorney, Agent, or Firm—Stephen J. Stark; Miller & Martin PLLC

(57) ABSTRACT

A connector head for a retractor blade provides connector head adapted to cooperate with a first and a second side loading socket. The connector head includes a first and a second loading portion, the second loading portion located above the first loading portion. A cap is preferably located between the first and second loading portions to separate the first and second loading portions from one another. The first loading portion includes a base which rests on a ledge surface of the retractor blade. The base and the cap may have sloped edges to assist in locating a socket between shoulders of the cap and base. The first loading portion has a diameter which is less than the diameter of the base an cap to define a first channel. The second loading portion has a smaller diameter than the diameter of the cap and top to provide a second channel. Two sockets from separate retractor instruments may connect to the connector head at the same time.

10 Claims, 1 Drawing Sheet

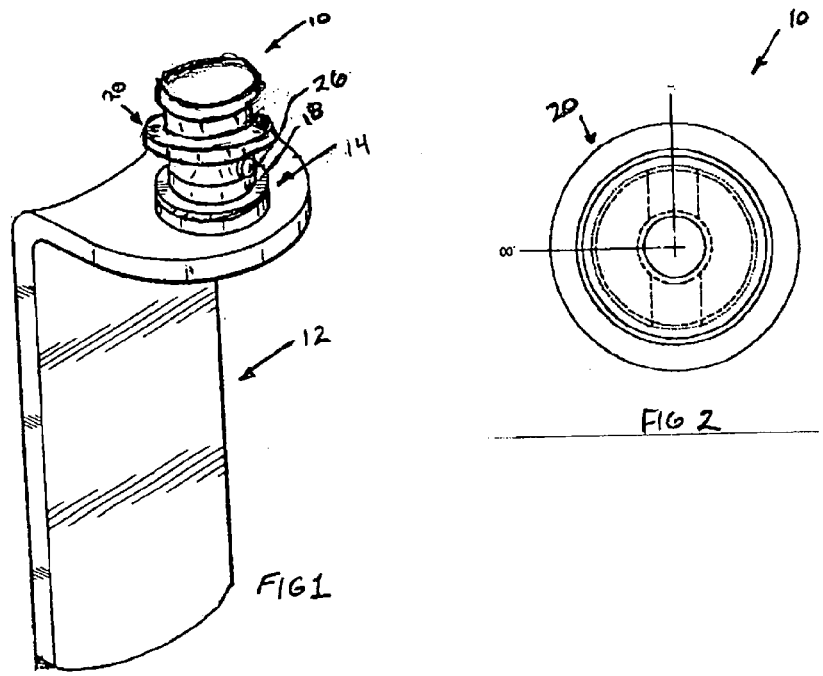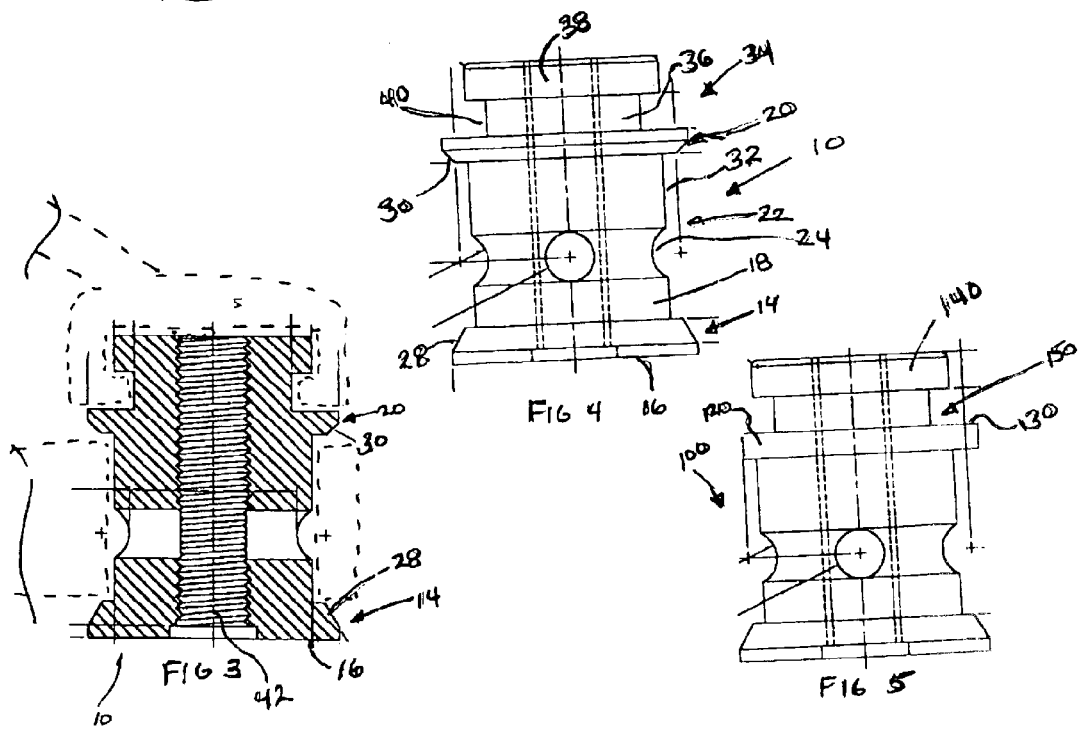

RETRACTOR BLADE CONNECTOR HEAD

CLAIM OF PRIORITY

This application claims the benefit of U.S. Provisional Patent Application No. 60/327,437 filed Oct. 5, 2001.

BACKGROUND OF THE INVENTION

1. Field of the Invention

The present invention relates generally to a connector head for use with a surgical retractor apparatus. More particular the present invention relates to a locking hub for use on a retractor blade.

2. Description of Related Art

When conducting some surgical procedures, it is often desirable to retract tissue. Although there are a number of procedures and devices available to retract tissue, U.S. Pat. No. 6,042,540 allows for the top loading as well as the side loading of retractor blades into a socket. The side loading feature of this, and other prior art, is believed to be advantageous whereby the surgeon's vision is not obscured while connecting, or disconnecting a blade from a retractor. The '540 Patent discloses a number of retractors which can utilize the blade of FIG. 1A, specifically, the longitudinal retractor of FIG. 3, the transverse retractor of FIG. 4, and the side-loading hand-held retractor of FIG. 5. Similar retractors are known in the art.

Although the retractor blade in the '540 Patent has a connector head that appears to work with sockets in the three different types of retractors disclosed, the connector head of the retractor blade is only adapted to work with one socket at a time. If the connector head is within a socket of one of the retractors, such as the hand-held retractor, it must first be removed from the first retractor before it may be inserted into a second retractor, such as the transverse retractor. Accordingly, the doctor will not be able to easily maintain traction force on the retractor blade during the switch from one retractor type to another.

SUMMARY OF THE INVENTION

A need exists for a retractor blade which may be held in position by one retractor type, such as a hand-held retractor, while connected to another retractor so that the blade is maintained with the desired traction force during the connection.

Another need exists for a connector head which facilitates the ability to have two retractors, each having respective sockets, to connect to the connector head at the same time.

Accordingly, a retractor blade includes a connector head adapted to cooperate with a first and a second side loading socket. The connector head includes a first and a second loading portion, the second loading portion located above the first loading portion. A cap is preferably located between the first and second loading portions to separate the first and second loading portions from one another.

The first loading portion includes a base which rests on a surface of the retractor blade. A first cylinder extends from the base to a cap. A groove may extend around a portion of the first cylinder to assist in connection with a socket. The base and the cap may have sloped edges to assist in locating a socket between shoulders of the cap and base. The first cylinder has a diameter which is preferably less than the diameter of the base and/or cap to provide a first channel. The first channel coordinates with a first socket to secure the connector head to a first retractor.

The second loading portion includes a second cylinder located between the cap and a top. The diameter of the cap and the top is preferably greater than the diameter of the second cylinder to provide a second channel. The second channel coordinates with a second socket to secure the connector head to a second retractor. One use of the two loading portion allows a user, such as a surgeon, to connect a second retractor, such as a hand-held retractor, to the connector head at the second loading position. The surgeon may then manipulate the retractor blade to a desired position with tissue retracted. With the retractor blade maintaining the tissue retracted, the first retractor may be connected to the first loading position and the second retractor disconnected from the retractor blade.

BRIEF DESCRIPTION OF THE DRAWINGS

The particular features and advantages of the invention as well as other objects will become apparent from the following description taken in connection with the accompanying drawings in which:

FIG. 1 shows a top perspective view of a retractor blade with a connector head of the present invention;

FIG. 2 is an top plan view of the connector head of FIG. 1 with some portions illustrated in phantom;

FIG. 3 is a cross sectional view of the connector head taken along the line A—A of FIG. 2 with sockets from two surgical instruments illustrated in phantom;

FIG. 4 is a side plan view of the connector head of FIG. 1 with some portions illustrated in phantom; and FIG. 5 is a side plan view of an alternative embodiment of a connector head with some portions illustrated in phantom.

DETAILED DESCRIPTION OF THE PREFERRED EMBODIMENT

FIGS. 1–4 illustrate a preferred connector head 10 for use with retractor blades 12 illustrated in FIG. 1. Retractor blades 12 of this type are known in the art. The illustrated blade 12 has a vertical tissue contact surface 13 connected to a horizontal flange 15. The flange 15 is substantially perpendicular to the tissue contact surface 13.

The connector head 10 is comprised of a base 14 which provides a connecting surface 16 for contacting blade 12. The connecting surface 16 is preferably planar to provide a secure connection between the blade 12 and the connector head 10. As illustrated, the base 14 connects at the flange 15 of the blade 12. A first cylinder 18 extends from the base 14 to a cap 20. The connector head 10 between the base 14 and cap 20 is the first loading portion 22. The first loading portion 22 includes the first cylinder 18, and preferably, a groove 24 and a locking pin 26. The locking pin 26 and/or the groove 24 may cooperate with a first socket of a first retractor (not shown). Retractors such as hand held retractors, transverse retractors, longitudinal retractors and others may have suitable first sockets for side loading into the first loading portion 22. Sockets are typically "U" shaped and may be capable of locking the first loading portion 22 therein.

In the preferred embodiment of FIGS. 1–4, both the base 14 and the cap 20 have sloped edge portions 28,30. These sloped edge portions 28,30 may assist in locating the first socket about at least a portion of the first loading position 22. The cap 20 has a greater radius than the radius of the first cylinder 18. The base is also illustrated having a greater radius than the radius of the first cylinder 18. Accordingly, a first channel 32 is created along the first cylinder 18 between the cap 20 and base 14.

Atop the cap 20 is located a second loading portion 34. The second loading portion 34 includes a second cylinder 36. A top 38 is preferably located atop the second cylinder 36 to assist in defining a second channel 40 since the top 38 and cap 20 have a greater radius than the second cylinder 36.

The second loading portion 34 allows for a user, such as a surgeon, to connect a second retractor socket of second retractor (not shown) to the second loading portion 34 and retract tissue of a patient to a desired position. While maintaining the tissue retracted, the first retractor portion 22 may be connected to a first retractor socket of a first retractor (not shown) which then maintains traction on the tissue as desired by the surgeon. The second retractor socket may then be removed from the second loading portion 34 to disconnect the second retractor from the connector head 10. It is envisioned that the preferred method of operation will be to utilize a hand held retractor with the second loading position 34, and a transverse retractor with the first loading position 22, however other methods could also be employed with the multiple loading positions 22,34.

The second loading portion 34 is preferably shorter than the first loading portion 22 which may be caused by the second cylinder 36 being shorter than the first cylinder 18. This provides the ability to have first and second sockets which are not interchangeable, which may be desirable in some applications. In addition to the first cylinder 18 being taller than the second cylinder 36, the first cylinder 18 is also illustrated having a larger radius than the second cylinder 36. Other size relationships between the first and second cylinders 18,36 may be desirable for particular uses.

In the embodiments illustrated in FIGS. 4 and 5, the second loading position 34 is envisioned to work with a second retractor for a relatively short period of time, such as to initially retract the tissue, while the first loading position 22 is configured to cooperate with a first retractor for a more extended time period. Other embodiments may have other needs and uses. Accordingly, grooves, pins and the like could be incorporated into the second loading position 34 as have been provided in the first loading position 22. In the preferred embodiment both the top 38 and the cap 20 prevent top loading of either of the first or second loading positions 22,34.

The second loading portion 34 may also function as a stabilizing platform for maintaining the connected retractor blade 12 in its correct location. The second loading portion 34 may also function as a stabilizing platform to maintain the first loading portion 22 in a first socket. These advantages may be achieved so that there is a reduced possibility of the head 10 from being disengaged from the side to side retraction forces.

The second loading portion 34 also reduces or eliminates the possibility of mislocating the head 10 to a first socket. The first socket (adapted to connect with first loading portion) is preferably selected so that it will not properly connect with the second loading portion 34.

FIGS. 2–4 show the connector head 10 with the pin 26, of FIG. 1, removed. Installation of pins 26 in connector heads 10 is known in the art, and the pin 26 is not necessary in all applications. FIG. 3 illustrates a threaded bore 42 extending through the connector head 10 to allow a bolt to extend through the blade 12 of FIG. 1 and into the connector head 10 to secure the base 14 of the connector head 10 to the blade 12.

The alternatively preferred embodiment of connector head 100 of FIG. 5 is similar to the embodiment shown in FIG. 1 except that cap 120 does not have a beveled edge 30 as illustrated in FIGS. 3 and 4. The cap has a landing surface 130 which is illustrated as a portion of the cap 120. The landing surface 130 has a larger radius than the top 140 to assist in connecting a second retractor socket to the second loading position 150. This feature has been found helpful in connecting a hand held retractor similar to the one disclosed in the '540 Patent to the second loading position 150.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A retractor blade connector head comprising:
   a base connected to a retractor blade;
   a cap spaced from the base;
   a first loading portion intermediate the base and the cap, said cap having a greater perimeter length than a perimeter length taken about the first loading portion defining a first channel intermediate the cap and base;
   a second loading portion extending upwardly above the cap, the perimeter length of said cap greater than a perimeter length taken about the second loading portion;
   a top located atop the second loading portion, said top having a perimeter length greater than the perimeter length of the second loading portion, said second loading portion defined as a channel intermediate the top and the cap, and the perimeter length of the cap greater than the perimeter length of the top; and
   sockets from two retractor instruments simultaneously connected to the connector head spaced apart by the cap.

2. The retractor blade connector head of claim 1 wherein the first loading portion is substantially cylindrical.

3. The retractor blade connector head of claim 2 wherein the second loading portion is substantially cylindrical.

4. The retractor blade connector head of claim 3 wherein the perimeter length of the cap corresponds to a circumference of the cap.

5. The retractor blade connector head of claim 1 wherein the cap has a sloped edge portion extending towards the first loading portion.

6. The retractor blade connector head of claim 1 wherein the base has a greater perimeter length than the perimeter length of the first loading portion.

7. The retractor blade connector head of claim 6 wherein the base has a sloped edge portion extending towards the first loading position.

8. The retractor blade connector head of claim 1 wherein the first loading portion has a groove about a first cylinder.

9. The retractor blade connector head of claim 1 wherein the retractor blade has a tissue contact surface perpendicular to a flange and the base connects to the flange.

10. A retractor blade connector head comprising:
    a base connected to a retractor blade;
    a cap spaced from the base;
    a first loading portion intermediate the base and the cap, said cap having a greater perimeter length than a perimeter length taken about the first loading portion defining a first channel intermediate the cap and base;
    a second loading portion extending upwardly above the cap, the perimeter length of said cap greater than a perimeter length taken about the second loading portion;
    a top located atop the second loading portion, said top having a perimeter length greater than the perimeter length of the second loading portion, said second loading portion defined as a channel intermediate the top and the cap, and the perimeter length of the cap greater than the perimeter length of the top; and
    a locking pin on the first loading portion.

* * * * *